United States Patent
Silvestri et al.

(10) Patent No.: US 7,547,321 B2
(45) Date of Patent: Jun. 16, 2009

(54) REMOVABLE STENT AND METHOD OF USING THE SAME

(75) Inventors: Gerard A. Silvestri, Mt. Pleasant, SC (US); Lutz Freitag, Hemer (DE)

(73) Assignee: Alveolus Inc., Charlotte, NC (US)

( * ) Notice: Subject to any disclaimer, the term of this patent is extended or adjusted under 35 U.S.C. 154(b) by 158 days.

(21) Appl. No.: 10/190,770

(22) Filed: Jul. 5, 2002

(65) Prior Publication Data
US 2003/0024534 A1 Feb. 6, 2003

Related U.S. Application Data

(60) Provisional application No. 60/308,071, filed on Jul. 26, 2001.

(51) Int. Cl.
*A61F 2/06* (2006.01)
*A61F 2/04* (2006.01)

(52) U.S. Cl. .................................... 623/1.15

(58) Field of Classification Search ................ 623/23.7, 623/1.15
See application file for complete search history.

(56) References Cited

U.S. PATENT DOCUMENTS

| | | | |
|---|---|---|---|
| 3,818,511 A | 6/1974 | Goldberg et al. | |
| 4,343,048 A | 8/1982 | Ross et al. | |
| 4,441,215 A | 4/1984 | Kaster | |
| 4,655,771 A | 4/1987 | Wallsten | |
| 4,665,906 A | 5/1987 | Jervis | |

(Continued)

FOREIGN PATENT DOCUMENTS

CA 2356911 7/2000

(Continued)

OTHER PUBLICATIONS

D.H. Kim et al., Evaluation of the Biodurability of Polyurethane Covered Stent Using a Flow Phantom, Korean J. Radiology, Jun. 2001: 2:75-79.

(Continued)

*Primary Examiner*—Alvin J Stewart
(74) *Attorney, Agent, or Firm*—Alston & Bird LLP

(57) ABSTRACT

The present invention, in an exemplary embodiment, provides a stent, which combines many of the excellent characteristics of both silicone and metal stents while eliminating the undesirable ones. In particular, it is an objective of a preferred embodiment of the present invention to provide a stent that is easily installed, yet removable. Moreover, the stent does not cause material infections and has the capacity to reduce infection. Therefore, a principal objective of a preferred embodiment in accordance with the present invention is to provide a prosthesis that is suitable for both permanent and temporary use while being easy to insert, reposition and remove. This prosthesis is also suitable for targeted delivery of antimicrobial and chemotherapeutic agents. Additionally, a principal objective in accordance with the present invention is to provide a family of stents where the relative hardness/softness of regions of the stent can differ from other regions of the stent to provide additional patient comfort and resistance to radial forces. An exemplary embodiment also provides a family of stents with novel interstice configurations that facilitate flexibility, durability and/or proper installation.

55 Claims, 6 Drawing Sheets

U.S. PATENT DOCUMENTS

| | | |
|---|---|---|
| 4,680,031 A | 7/1987 | Alonso |
| 4,733,665 A | 3/1988 | Palmaz |
| 4,739,762 A | 4/1988 | Palmaz |
| 4,743,251 A | 5/1988 | Barra |
| 4,800,882 A | 1/1989 | Gianturco |
| 4,820,262 A | 4/1989 | Finney |
| 4,820,298 A | 4/1989 | Leveen et al. |
| 4,856,516 A | 8/1989 | Hillstead |
| 4,886,062 A | 12/1989 | Wiktor |
| 5,032,128 A | 7/1991 | Alonso |
| 5,061,275 A | 10/1991 | Wallsten et al. |
| 5,064,435 A | 11/1991 | Porter |
| 5,067,957 A | 11/1991 | Jervis |
| 5,073,694 A | 12/1991 | Tessier et al. |
| 5,102,417 A | 4/1992 | Palmaz |
| 5,104,404 A | 4/1992 | Wolff |
| 5,190,546 A | 3/1993 | Jervis |
| 5,195,984 A | 3/1993 | Schatz |
| 5,229,431 A | 7/1993 | Pinchuk |
| 5,292,331 A | 3/1994 | Boneau |
| 5,345,057 A | 9/1994 | Muller |
| 5,354,309 A | 10/1994 | Schnepp-Pesch et al. |
| 5,356,423 A | 10/1994 | Tihon et al. |
| 5,383,892 A | 1/1995 | Cardon et al. |
| 5,383,925 A | 1/1995 | Schmitt |
| 5,421,955 A * | 6/1995 | Lau et al. .................... 216/48 |
| 5,433,723 A | 7/1995 | Lindenberg et al. |
| 5,443,498 A | 8/1995 | Fontaine |
| 5,449,373 A | 9/1995 | Pinchasik et al. |
| 5,480,431 A | 1/1996 | Frietag et al. |
| 5,514,154 A | 5/1996 | Lau et al. |
| 5,520,697 A | 5/1996 | Lindenberg et al. |
| 5,534,287 A | 7/1996 | Lukic |
| 5,540,713 A | 7/1996 | Schnepp-Pesch et al. |
| 5,562,725 A | 10/1996 | Schmitt et al. |
| 5,575,818 A | 11/1996 | Pinchuk |
| 5,591,157 A | 1/1997 | Hennings et al. |
| 5,591,197 A | 1/1997 | Orth et al. |
| 5,593,442 A | 1/1997 | Klein |
| 5,597,378 A | 1/1997 | Jervis |
| 5,601,593 A | 2/1997 | Freitag |
| 5,609,629 A | 3/1997 | Fearnot et al. |
| 5,618,301 A | 4/1997 | Hauenstein et al. |
| 5,628,788 A | 5/1997 | Pinchuk |
| 5,643,312 A | 7/1997 | Fischell et al. |
| 5,645,559 A | 7/1997 | Hachtman et al. |
| 5,662,713 A | 9/1997 | Andersen et al. |
| 5,667,486 A | 9/1997 | Mikulich et al. |
| 5,674,241 A | 10/1997 | Bley et al. |
| 5,681,346 A | 10/1997 | Orth et al. |
| 5,697,971 A | 12/1997 | Fischell et al. |
| 5,707,386 A | 1/1998 | Schnepp-Pesch et al. |
| 5,713,949 A | 2/1998 | Jayaraman |
| 5,716,393 A | 2/1998 | Lindenberg et al. |
| 5,725,572 A | 3/1998 | Lam et al. |
| 5,733,303 A | 3/1998 | Israel et al. |
| 5,741,333 A | 4/1998 | Frid |
| 5,755,776 A | 5/1998 | Al-Saadon |
| 5,755,781 A | 5/1998 | Jayaraman |
| 5,759,192 A | 6/1998 | Saunders |
| 5,766,238 A | 6/1998 | Lau et al. |
| 5,776,161 A | 7/1998 | Globerman |
| 5,780,807 A | 7/1998 | Saunders |
| 5,807,404 A | 9/1998 | Richter |
| 5,814,063 A | 9/1998 | Freitag |
| 5,824,042 A | 10/1998 | Lombardi et al. |
| 5,827,321 A | 10/1998 | Roubin et al. |
| 5,833,707 A | 11/1998 | McIntyre et al. |
| 5,836,966 A | 11/1998 | St. Germain |
| 5,837,313 A | 11/1998 | Ding et al. |
| 5,843,120 A | 12/1998 | Israel et al. |
| 5,853,419 A * | 12/1998 | Imran ........................ 623/1.15 |
| 5,860,998 A | 1/1999 | Robinson et al. |
| 5,860,999 A | 1/1999 | Schnepp-Pesch et al. |
| 5,873,904 A | 2/1999 | Ragheb et al. |
| 5,876,418 A | 3/1999 | Hauenstein et al. |
| 5,876,445 A | 3/1999 | Andersen et al. |
| 5,876,448 A | 3/1999 | Thompson et al. |
| 5,876,449 A | 3/1999 | Starck et al. |
| 5,879,370 A | 3/1999 | Fischell et al. |
| 5,902,475 A | 5/1999 | Trozera et al. |
| 5,911,732 A | 6/1999 | Hojeibane |
| 5,922,019 A | 7/1999 | Hankh et al. |
| 5,922,020 A | 7/1999 | Klein et al. |
| 5,922,393 A | 7/1999 | Jayaraman |
| 5,931,866 A | 8/1999 | Frantzen |
| 5,935,162 A | 8/1999 | Dang |
| 5,938,682 A | 8/1999 | Hojeibane et al. |
| 5,968,070 A | 10/1999 | Bley et al. |
| 5,968,091 A | 10/1999 | Pinchuk et al. |
| 5,971,950 A | 10/1999 | Lopez et al. |
| 5,972,018 A | 10/1999 | Israel et al. |
| 5,980,552 A | 11/1999 | Pinchasik et al. |
| 6,017,365 A | 1/2000 | Von Oepen |
| 6,022,371 A | 2/2000 | Killion |
| 6,027,527 A | 2/2000 | Asano et al. |
| 6,033,435 A | 3/2000 | Penn et al. |
| 6,042,597 A | 3/2000 | Kveen et al. |
| 6,048,361 A | 4/2000 | Von Oepen |
| 6,051,021 A | 4/2000 | Frid |
| 6,053,941 A | 4/2000 | Lindenberg et al. |
| 6,056,775 A | 5/2000 | Borghi et al. |
| 6,059,811 A | 5/2000 | Pinchasik et al. |
| 6,096,070 A | 8/2000 | Ragheb et al. |
| 6,099,560 A | 8/2000 | Penn et al. |
| 6,106,548 A | 8/2000 | Roubin et al. |
| 6,120,534 A | 9/2000 | Ruiz |
| 6,131,266 A | 10/2000 | Saunders |
| 6,132,461 A | 10/2000 | Thompson |
| 6,136,006 A | 10/2000 | Johnson et al. |
| 6,136,022 A | 10/2000 | Nunez et al. |
| 6,146,403 A | 11/2000 | St. Germain |
| 6,146,416 A | 11/2000 | Andersen et al. |
| 6,156,052 A | 12/2000 | Richter et al. |
| 6,159,238 A | 12/2000 | Killion et al. |
| 6,159,239 A | 12/2000 | Greenhalgh |
| 6,171,334 B1 | 1/2001 | Cox |
| 6,174,329 B1 | 1/2001 | Callol et al. |
| 6,179,867 B1 | 1/2001 | Cox |
| 6,183,506 B1 | 2/2001 | Penn et al. |
| 6,190,407 B1 * | 2/2001 | Ogle et al. ................. 623/1.51 |
| 6,193,744 B1 | 2/2001 | Ehr et al. |
| 6,203,568 B1 | 3/2001 | Lombardi et al. |
| 6,206,916 B1 | 3/2001 | Furst |
| 6,217,608 B1 | 4/2001 | Penn et al. |
| 6,231,598 B1 | 5/2001 | Berry et al. |
| 6,231,599 B1 | 5/2001 | Ley |
| 6,241,760 B1 | 6/2001 | Jang |
| 6,248,058 B1 | 6/2001 | Silverman et al. |
| 6,251,134 B1 | 6/2001 | Alt et al. |
| 6,258,121 B1 | 7/2001 | Yang et al. |
| 6,270,524 B1 | 8/2001 | Kim |
| 6,273,910 B1 | 8/2001 | Limon |
| 6,283,992 B1 | 9/2001 | Hankh et al. |
| 6,293,964 B1 | 9/2001 | Yadav |
| 6,293,966 B1 | 9/2001 | Frantzen |
| 6,293,968 B1 | 9/2001 | Taheri |
| 6,306,141 B1 | 10/2001 | Jervis |
| 6,312,459 B1 | 11/2001 | Huang et al. |
| 6,315,794 B1 | 11/2001 | Richter |
| 6,325,821 B1 | 12/2001 | Gaschino et al. |
| 6,325,825 B1 | 12/2001 | Kula et al. |
| 6,336,938 B1 | 1/2002 | Kavteladze et al. |
| 6,348,065 B1 | 2/2002 | Brown et al. |

| Patent | Kind | Date | Inventor |
|---|---|---|---|
| 6,352,552 | B1 | 3/2002 | Levinson et al. |
| 6,355,063 | B1 | 3/2002 | Calcote |
| 6,361,557 | B1 | 3/2002 | Gittings et al. |
| 6,375,676 | B1 | 4/2002 | Cox |
| 6,375,677 | B1 | 4/2002 | Penn et al. |
| 6,380,457 | B1 | 4/2002 | Yurek et al. |
| 6,395,020 | B1 | 5/2002 | Ley et al. |
| 6,409,750 | B1 | 6/2002 | Hyodoh et al. |
| 6,409,754 | B1 | 6/2002 | Smith et al. |
| 6,416,538 | B1 | 7/2002 | Ley et al. |
| 6,420,378 | B1 * | 7/2002 | Rubinfeld .................. 514/283 |
| 6,423,084 | B1 | 7/2002 | St. Germain |
| 6,423,091 | B1 | 7/2002 | Hojeibane |
| 6,428,570 | B1 | 8/2002 | Globerman |
| 6,432,133 | B1 | 8/2002 | Lau et al. |
| 6,436,133 | B1 * | 8/2002 | Furst et al. ................ 623/1.15 |
| 6,440,162 | B1 | 8/2002 | Cox et al. |
| 6,443,982 | B1 | 9/2002 | Israel et al. |
| 6,451,049 | B2 | 9/2002 | Vallana et al. |
| 6,461,380 | B1 | 10/2002 | Cox |
| 6,461,381 | B2 | 10/2002 | Israel et al. |
| 6,464,720 | B2 | 10/2002 | Boatman et al. |
| 6,464,722 | B2 | 10/2002 | Israel et al. |
| 6,471,721 | B1 | 10/2002 | Dang |
| 6,475,234 | B1 | 11/2002 | Richter et al. |
| 6,475,236 | B1 | 11/2002 | Roubin et al. |
| 6,478,815 | B1 | 11/2002 | Alt |
| 6,488,703 | B1 | 12/2002 | Kveen et al. |
| 6,508,834 | B1 | 1/2003 | Pinchasik et al. |
| 6,514,285 | B1 | 2/2003 | Pinchasik |
| 6,533,805 | B1 | 3/2003 | Jervis |
| 6,533,810 | B2 | 3/2003 | Hankh et al. |
| 6,540,777 | B2 | 4/2003 | Stenzel |
| 6,551,351 | B2 | 4/2003 | Smith et al. |
| 6,569,194 | B1 | 5/2003 | Pelton |
| 6,572,646 | B1 | 6/2003 | Boylan et al. |
| 6,589,276 | B2 | 7/2003 | Pinchasik et al. |
| 6,602,285 | B1 | 8/2003 | Von Oepen et al. |
| 6,613,078 | B1 | 9/2003 | Barone |
| 6,613,079 | B1 | 9/2003 | Wolinsky et al. |
| 6,613,080 | B1 | 9/2003 | Lootz |
| 6,613,081 | B2 | 9/2003 | Kim et al. |
| 6,616,688 | B2 | 9/2003 | Von Oepen |
| 6,616,689 | B1 | 9/2003 | Ainsworth et al. |
| 6,616,690 | B2 | 9/2003 | Rolando et al. |
| 6,620,192 | B1 | 9/2003 | Jalisi |
| 6,620,193 | B1 | 9/2003 | Lau et al. |
| 6,620,201 | B1 | 9/2003 | Nadal et al. |
| 6,623,518 | B2 * | 9/2003 | Thompson et al. ......... 623/1.11 |
| 6,623,520 | B2 | 9/2003 | Jalisi |
| 6,629,994 | B2 | 10/2003 | Gomez et al. |
| 6,635,084 | B2 | 10/2003 | Israel et al. |
| 6,638,293 | B1 | 10/2003 | Makower et al. |
| 6,638,300 | B1 | 10/2003 | Frantzen |
| 6,638,302 | B1 | 10/2003 | Curcio et al. |
| 6,641,607 | B1 | 11/2003 | Hossainy et al. |
| 6,641,608 | B1 | 11/2003 | Pulnev |
| 6,641,609 | B2 | 11/2003 | Globerman |
| 6,641,611 | B2 | 11/2003 | Jayaraman |
| 6,645,240 | B2 | 11/2003 | Yee |
| 6,645,242 | B1 | 11/2003 | Quinn |
| 6,652,572 | B2 | 11/2003 | Kugler et al. |
| 6,652,573 | B2 | 11/2003 | Von Oepen |
| 6,652,575 | B2 | 11/2003 | Wang |
| 6,652,579 | B1 | 11/2003 | Cox et al. |
| 6,653,426 | B2 | 11/2003 | Alvarado et al. |
| 6,656,201 | B2 | 12/2003 | Ferrera et al. |
| 6,656,214 | B1 | 12/2003 | Fogarty et al. |
| 6,656,216 | B1 | 12/2003 | Hossainy et al. |
| 6,656,217 | B1 | 12/2003 | Herzog, Jr. et al. |
| 6,656,220 | B1 | 12/2003 | Gomez et al. |
| 6,656,351 | B2 | 12/2003 | Boyle |
| 6,660,019 | B1 | 12/2003 | Richter et al. |
| 6,660,030 | B2 | 12/2003 | Shaolian et al. |
| 6,660,034 | B1 | 12/2003 | Mandrusov et al. |
| 6,660,827 | B2 | 12/2003 | Loomis et al. |
| 6,663,664 | B1 | 12/2003 | Pacetti |
| 6,664,335 | B2 | 12/2003 | Krishnan |
| 6,666,881 | B1 | 12/2003 | Richter et al. |
| 6,666,884 | B1 | 12/2003 | Webster |
| 6,669,721 | B1 | 12/2003 | Bose et al. |
| 6,669,722 | B2 | 12/2003 | Chen et al. |
| 6,669,723 | B2 | 12/2003 | Killion et al. |
| 6,673,102 | B1 | 1/2004 | Vonesh et al. |
| 6,673,103 | B1 | 1/2004 | Golds et al. |
| 6,673,104 | B2 | 1/2004 | Barry |
| 6,673,105 | B1 | 1/2004 | Chen |
| 6,673,106 | B2 | 1/2004 | Mitelberg et al. |
| 6,673,107 | B1 | 1/2004 | Brandt et al. |
| 6,673,154 | B1 | 1/2004 | Pacetti et al. |
| 6,676,697 | B1 | 1/2004 | Richter |
| 6,679,910 | B1 | 1/2004 | Granada |
| 6,679,911 | B2 | 1/2004 | Burgermeister |
| 6,682,554 | B2 | 1/2004 | Oepen et al. |
| 6,685,736 | B1 | 2/2004 | White et al. |
| 6,685,745 | B2 | 2/2004 | Reever |
| 6,689,158 | B1 | 2/2004 | White et al. |
| 6,689,162 | B1 | 2/2004 | Thompson |
| 6,692,483 | B2 | 2/2004 | Vardi et al. |
| 6,692,521 | B2 | 2/2004 | Pinchasik |
| 6,692,522 | B1 | 2/2004 | Richter |
| 6,695,833 | B1 | 2/2004 | Frantzen |
| 6,695,876 | B1 | 2/2004 | Marotta et al. |
| 6,699,276 | B2 | 3/2004 | Sogard et al. |
| 6,699,278 | B2 | 3/2004 | Fischell et al. |
| 6,706,061 | B1 | 3/2004 | Fischell et al. |
| 6,706,062 | B2 | 3/2004 | Vardi et al. |
| 6,709,440 | B2 | 3/2004 | Callol et al. |
| 6,709,451 | B1 | 3/2004 | Noble et al. |
| 6,709,453 | B2 | 3/2004 | Pinchasik et al. |
| 6,709,454 | B1 | 3/2004 | Cox et al. |
| 6,712,843 | B2 | 3/2004 | Elliott |
| 6,712,844 | B2 | 3/2004 | Pacetti |
| 6,712,846 | B1 | 3/2004 | Kraus et al. |
| 6,716,240 | B2 | 4/2004 | Fischell et al. |
| 6,719,782 | B1 | 4/2004 | Chuter |
| 6,719,991 | B2 * | 4/2004 | Darouiche et al. .......... 424/422 |
| 6,723,118 | B2 | 4/2004 | Ballou et al. |
| 6,723,119 | B2 | 4/2004 | Pinchasik et al. |
| 6,723,120 | B2 | 4/2004 | Yan |
| 6,723,121 | B1 | 4/2004 | Zhong |
| 6,723,373 | B1 | 4/2004 | Narayanan et al. |
| 6,730,064 | B2 | 5/2004 | Ragheb et al. |
| 6,730,116 | B1 | 5/2004 | Wolinsky et al. |
| 6,730,117 | B1 | 5/2004 | Tseng et al. |
| 6,730,120 | B2 | 5/2004 | Berg et al. |
| 6,733,523 | B2 | 5/2004 | Shaolian et al. |
| 6,733,524 | B2 | 5/2004 | Tseng et al. |
| 6,736,838 | B1 | 5/2004 | Richter |
| 6,736,843 | B1 | 5/2004 | Fariabi |
| 6,736,844 | B1 | 5/2004 | Glatt et al. |
| 6,740,113 | B2 | 5/2004 | Vrba |
| 6,740,114 | B2 | 5/2004 | Burgermeister |
| 6,740,115 | B2 | 5/2004 | Lombardi et al. |
| 6,743,252 | B1 | 6/2004 | Bates et al. |
| 6,746,475 | B1 | 6/2004 | Rivelli, Jr. |
| 6,746,476 | B1 | 6/2004 | Hojeibane |
| 6,746,477 | B2 | 6/2004 | Moore |
| 6,746,479 | B2 | 6/2004 | Ehr et al. |
| 6,746,482 | B2 | 6/2004 | Ung-Chhun |
| 6,749,629 | B1 | 6/2004 | Hong et al. |
| 6,752,826 | B2 | 6/2004 | Holloway et al. |
| 6,752,829 | B2 | 6/2004 | Kocur et al. |
| 6,753,071 | B1 | 6/2004 | Pacetti |
| 6,755,856 | B2 | 6/2004 | Fierens et al. |
| 6,756,007 | B2 | 6/2004 | Pletzer et al. |

| | | | | | | |
|---|---|---|---|---|---|---|
| 6,758,858 | B2 | 7/2004 | McCrea et al. | 7,004,966 B2 | 2/2006 | Edwin et al. |
| 6,758,859 | B1 | 7/2004 | Dang et al. | 2001/0000043 A1 | 3/2001 | Israel et al. |
| 6,758,860 | B1 | 7/2004 | Penn et al. | 2001/0005793 A1 | 6/2001 | Brenneman |
| 6,761,731 | B2 | 7/2004 | Majercak | 2001/0016767 A1 | 8/2001 | Wilson et al. |
| 6,764,505 | B1 | 7/2004 | Hossainy et al. | 2001/0016768 A1 | 8/2001 | Wilson et al. |
| 6,764,506 | B2 | 7/2004 | Roubin et al. | 2001/0027339 A1 | 10/2001 | Boatman et al. |
| 6,764,507 | B2 | 7/2004 | Shanley et al. | 2001/0037138 A1 | 11/2001 | Wilson et al. |
| 6,764,519 | B2 | 7/2004 | Whitmore, III | 2002/0002396 A1 | 1/2002 | Fulkerson |
| 6,770,086 | B1 | 8/2004 | Girton | 2002/0002399 A1 | 1/2002 | Huxel et al. |
| 6,770,088 | B1 | 8/2004 | Jang | 2002/0042650 A1 | 4/2002 | Vardi et al. |
| 6,770,089 | B1 | 8/2004 | Hong et al. | 2002/0045933 A1 | 4/2002 | Jang |
| 6,770,091 | B2 | 8/2004 | Richter et al. | 2002/0111672 A1 | 8/2002 | Kim et al. |
| 6,773,445 | B2 | 8/2004 | Finlay et al. | 2002/0156524 A1 | 10/2002 | Ehr et al. |
| 6,774,157 | B2 | 8/2004 | DelMain | 2002/0183831 A1 | 12/2002 | Rolando et al. |
| 6,774,278 | B1 | 8/2004 | Ragheb et al. | 2002/0183832 A1 | 12/2002 | Penn et al. |
| 6,776,022 | B2 | 8/2004 | Kula et al. | 2002/0193866 A1 | 12/2002 | Saunders |
| 6,776,792 | B1 | 8/2004 | Yan et al. | 2002/0198593 A1 | 12/2002 | Gomez et al. |
| 6,776,793 | B2 | 8/2004 | Brown et al. | 2003/0004567 A1 | 1/2003 | Boyle et al. |
| 6,776,794 | B1 | 8/2004 | Hong et al. | 2003/0028240 A1 | 2/2003 | Nolting et al. |
| 6,776,795 | B2 | 8/2004 | Pelton | 2003/0036793 A1 | 2/2003 | Richter et al. |
| 6,776,796 | B2 | 8/2004 | Falotico et al. | 2003/0045925 A1 | 3/2003 | Jayaraman |
| 6,786,929 | B2 | 9/2004 | Gambale et al. | 2003/0050690 A1 | 3/2003 | Kveen et al. |
| 6,790,222 | B2 | 9/2004 | Kugler et al. | 2003/0077310 A1 | 4/2003 | Pathak et al. |
| 6,790,227 | B2 | 9/2004 | Burgermeister | 2003/0083734 A1 | 5/2003 | Friedrich et al. |
| 6,790,228 | B2 | 9/2004 | Hossainy et al. | 2003/0105511 A1 | 6/2003 | Welsh et al. |
| 6,796,997 | B1 | 9/2004 | Penn et al. | 2003/0105513 A1 | 6/2003 | Moriuchi et al. |
| 6,797,217 | B2 | 9/2004 | McCrea et al. | 2003/0114919 A1 | 6/2003 | McQuiston et al. |
| 6,800,089 | B1 | 10/2004 | Wang | 2003/0125799 A1 | 7/2003 | Limon |
| 6,802,859 | B1 | 10/2004 | Pazienza et al. | 2003/0139796 A1 | 7/2003 | Sequin et al. |
| 6,805,702 | B1 | 10/2004 | Chen et al. | 2003/0139803 A1 | 7/2003 | Sequin et al. |
| 6,805,703 | B2 | 10/2004 | McMorrow | 2003/0144726 A1 | 7/2003 | Majercak et al. |
| 6,805,704 | B1 | 10/2004 | Hoyns | 2003/0144731 A1 | 7/2003 | Wolinsky et al. |
| 6,805,705 | B2 * | 10/2004 | Hong et al. ............... 623/1.15 | 2003/0149469 A1 | 8/2003 | Wolinsky et al. |
| 6,805,706 | B2 | 10/2004 | Solovay et al. | 2003/0158596 A1 | 8/2003 | Ikeuchi et al. |
| 6,805,707 | B1 | 10/2004 | Hong et al. | | | |
| 6,805,709 | B1 | 10/2004 | Schaldach et al. | | FOREIGN PATENT DOCUMENTS | |
| 6,805,898 | B1 | 10/2004 | Wu et al. | DE | 299 04 817 | 7/1999 |
| 6,808,533 | B1 | 10/2004 | Goodwin et al. | DE | 199 06 956 | 8/2000 |
| 6,814,749 | B2 | 11/2004 | Cox et al. | DE | 199 06 956 A 1 | 8/2000 |
| 6,818,013 | B2 | 11/2004 | Mitelberg et al. | DE | 199 37 638 A 1 | 5/2001 |
| 6,818,014 | B2 | 11/2004 | Brown et al. | EP | 0 183 372 | 10/1984 |
| 6,818,015 | B2 | 11/2004 | Hankh et al. | EP | 0 350 302 | 1/1990 |
| 6,818,247 | B1 | 11/2004 | Chen et al. | EP | 0 378 151 A2 | 7/1990 |
| 6,821,291 | B2 | 11/2004 | Bolea et al. | EP | 0 540 290 A2 | 10/1991 |
| 6,821,292 | B2 | 11/2004 | Pazienza et al. | EP | 0 540 290 A2 | 5/1993 |
| 6,821,293 | B2 | 11/2004 | Pinchasik | EP | 0 621 015 A1 | 10/1994 |
| 6,830,638 | B2 | 12/2004 | Boylan et al. | EP | 0 797 963 A2 | 1/1997 |
| 6,833,004 | B2 | 12/2004 | Ishii et al. | EP | 0 792 627 A2 | 3/1997 |
| 6,843,802 | B1 | 1/2005 | Villalobos et al. | EP | 0 945 107 A2 | 1/1999 |
| 6,849,086 | B2 | 2/2005 | Cragg | EP | 1 088 528 | 4/2001 |
| 6,852,124 | B2 | 2/2005 | Cox et al. | EP | 1 093 771 A2 | 4/2001 |
| 6,858,037 | B2 | 2/2005 | Penn et al. | EP | 1 208 814 A2 | 9/2001 |
| 6,860,898 | B2 | 3/2005 | Stack et al. | EP | 1 151 730 A2 | 11/2001 |
| 6,860,900 | B2 | 3/2005 | Clerc et al. | EP | 1 197 188 A2 | 4/2002 |
| 6,863,684 | B2 | 3/2005 | Kim et al. | EP | 1 290 984 A2 | 12/2003 |
| 6,866,805 | B2 | 3/2005 | Hong et al. | FR | 2 758 253 | 7/1998 |
| 6,875,227 | B2 | 4/2005 | Yoon | JP | 2002-102251 | 4/2002 |
| 6,878,162 | B2 | 4/2005 | Bales et al. | JP | 2002-345971 | 12/2002 |
| 6,881,221 | B2 | 4/2005 | Golds | WO | WO 91/13384 | 9/1991 |
| 6,881,222 | B2 | 4/2005 | White et al. | WO | WO 92/11824 | 7/1992 |
| 6,881,223 | B2 | 4/2005 | Penn et al. | WO | WO 93/22986 | 11/1993 |
| 6,887,264 | B2 | 5/2005 | Penn et al. | WO | WO 94/04096 | 3/1994 |
| 6,896,696 | B2 | 5/2005 | Doran et al. | WO | WO 94/21196 | 9/1994 |
| 6,896,697 | B1 | 5/2005 | Yip et al. | WO | WO 97/07751 | 3/1997 |
| 6,896,698 | B2 | 5/2005 | Rolando et al. | WO | WO 97/10011 | 3/1997 |
| 6,899,729 | B1 | 5/2005 | Cox et al. | WO | WO 98/19628 | 5/1998 |
| 6,908,624 | B2 | 6/2005 | Hossainy et al. | WO | WO 99/02105 | 1/1999 |
| 6,911,041 | B1 | 6/2005 | Zschecg | WO | WO 99/40876 | 8/1999 |
| 6,916,336 | B2 | 7/2005 | Patel et al. | WO | WO 99/62430 | 12/1999 |
| 6,920,677 | B2 | 7/2005 | Dolan et al. | WO | WO 00/09041 | 2/2000 |
| 6,955,723 | B2 | 10/2005 | Pacetti et al. | WO | WO 00/44309 | 8/2000 |
| 6,979,348 | B2 | 12/2005 | Sundar | WO | WO 00/45742 | 8/2000 |
| 6,997,946 | B2 * | 2/2006 | Girton et al. ............... 623/1.15 | | | |

| | | |
|---|---|---|
| WO | WO 01/76508 A2 | 10/2001 |
| WO | WO 01/76508 A3 | 10/2001 |
| WO | WO 02/19948 A2 | 3/2002 |

OTHER PUBLICATIONS

U.S. Appl. No. 08/246,320, filed May 19, 1994, Burnmeister et al.

Search Report from corresponding European Application No. 02749974.8.

Examination Report for corresponding Canadian Patent Appl. No. 2,454,871, completed Feb. 27, 2007.

PCT International Search Report mailed May 12, 2003 for PCT/US02/22098.

* cited by examiner

REMOVABLE STENT AND METHOD OF USING THE SAME

This patent application claims the benefit of priority under 35 U.S.C. § 119 to U.S. Provisional Application Ser. No. 60/308,071, filed Jul. 26, 2001.

FIELD OF THE INVENTION

The present invention relates generally to medical devices directed to the prevention of nonvascular vessel or passageway occlusion, and more particularly to removable tracheal/bronchial stents and methods for utilizing these stents in the treatment of both benign and malignant conditions.

BACKGROUND OF THE INVENTION

Stents are devices that are inserted into a vessel or passage to keep the lumen open and prevent closure due to a stricture, external compression, or internal obstruction. In particular, stents are commonly used to keep blood vessels open in the coronary arteries and they are frequently inserted into the ureters to maintain drainage from the kidneys, the bile duct for pancreatic cancer or cholangiocarcinoma or the esophagus for strictures or cancer.

In particular, airway stents are principally utilized for four indications, namely: (1) re-establishment of airway patency due to extrinsic tracheobronchial compression from either mass or lymph nodes; (2) re-establishment of airway patency due to intrinsic tracheobronchial obstruction from malignant or benign disease; (3) to cover a fistula track secondary to tracheo-esophageal fistula; and/or (4) to maintain airway patency in patients with tracheobronchial malacia. There are currently two basic types of stents available for some but not all of these indications: polymer or metal.

In 1990 a silicone stent developed by Dumon was reported upon in the medical literature, it is currently the most widely utilized stent in the world. The primary advantage of the silicone stent is its removability. However, this stent must be placed through a rigid metal tube (rigid bronchoscopy), in an operating suite, under general anesthesia, which increases the cost of the procedure and potentially places the patient at greater risk for complications. This technique requires extensive training and is only performed at specialized centers. The Dumon stent is thick-walled, which increases airway resistance and decreases mucociliary clearance. This problem leads to mucous impaction and tracheobronchitis. Additionally, these polymer stents are of fixed luminal diameter and do not self expand to meet the changing contour of the airway. This leads to a problem with stent migration. The cylindrical tube design does not conform to curved or conical airway anatomy and they also cause the formation of granulation tissue, which results from airway irritation.

In light of these disadvantages, and at the expense of removability, industry has moved away from the polymer stent in favor of the self-expanding metal stent. The two most widely used are the ultraflex and wall stent, which have shape memory characteristics. They are self-expanding and can be placed through a flexible bronchoscope, under conscious sedation, using local anesthesia in an outpatient setting. They have sufficient wall to lumen ratio, minimal interference with mucociliary clearance and conform to difficult airway anatomy. Unfortunately, after approximately six weeks, the wire mesh in these stents becomes epithelialized, thus making removal difficult, if not impossible.

Rejection of the stent can occur with severe airway irritation and tracheobronchitis that is impossible to treat because the nidus for the infection is the metal, which cannot be removed. Because of the inability to remove these stents, they are indicated only as a last resort for benign disease. Additionally, these stents can be challenging to deploy because they can elongate or foreshorten, depending upon the diameter of the airway.

An additional disadvantage of conventional metal stents is that they can migrate, like polymer stents, since the axial working length of these stents varies when the stent is radially compressed. Attempts have been made to address this problem by providing a stent that is comprised of knit layers of metal to form a wire mesh with peristaltic capabilities. Unfortunately, by preparing a stent from twisted wire portions, the likelihood of tissue aggravation increases because the weaved loops of the stent dislocate when subjected to radial compression. Moreover, for certain stents, sharp edges exist at the final loop ends.

As a result, physicians have the intractable dilemma of having to decide whether the patient should undergo the intricate procedure to receive the removable polymer stent, which can migrate and/or cause granulation tissue formation, and is subject to recurrent infections. Though the metal stent is easier to implant, the risk of infection and granulation tissue formation is not reduced because the stents become epithelialized and, therefore, impossible to remove.

An additional limitation of conventional stents is the inability to adapt a single design to diverse locations of the patient's anatomy. For example, as a result of differences in topology, physicians are generally required to find different devices from different manufacturers to address conditions in varying parts of the patient's anatomy. A uniform design and method of implantation while still allowing for the shape and resiliency modification necessary to accommodate the intricacies of various lumens throughout the body would be advantageous. Therefore, there is a need for a uniform prosthesis or family of related devices that can address various anatomical challenges while allowing the physician to develop a comfort level with a particular product design and implantation method.

Therefore, there also remains an existing need for a prosthesis that is; removable, prevents epithelialization thereof, does not migrate, and is suitably configured to minimize infections and airway irritation. This is of principal importance because in tracheobronchial stenting, unlike other lumens in the body, the airway is constantly exposed to inhaled bacteria thus increasing the risk of infection. However, there is a need for a prosthesis that carries the above advantages while being suitable for use in a wide variety of anatomic locations within a patient. The configuration must also facilitate a method of introduction that prevents the premature elongation and foreshortening of the stent while suitably engaging the desired implantation location. The stent must also retain its axial length while undergoing radial compression. Moreover, there is an existing need for a stent that has both antimicrobial and chemotherapeutic properties so that the stent can be indicated as an early stage therapy.

There is an existing need for a prosthesis that is designed to accommodate varying tissue types in lumens of the body. In particular, there is a need for a family of stents where the relative hardness/softness of regions of the stent can differ from other regions of the stent to provide additional patient comfort and resistance to radial forces. There is also an existing need for a family of stents with novel interstice configurations that facilitate flexibility, durability and/or proper installation. Presently, there is a need for a self-expanding stent have the above benefits that also defines a plurality of apertures at the termini of the stent for, inter alia, removal of the stent.

SUMMARY OF EXEMPLARY EMBODIMENTS

It is a principal purpose of the present invention to provide a stent, in accordance with an exemplary embodiment of the present invention, which combines many of the excellent characteristics of both silicone and metal stents while eliminating the undesirable ones. In particular, it is an objective of a preferred embodiment in accordance with the present invention to provide a stent that is easily installed, yet removable. Moreover the stent in accordance with this embodiment of the present invention would not cause material infections and may be capable of reducing infection. Therefore, a principal objective of a preferred embodiment in accordance with the present invention is to provide a prosthesis that is suitable for both permanent and temporary use while being easy to insert, reposition and remove.

Another principal objective in accordance with a preferred embodiment of the present invention is to provide a tracheal/bronchial stent that is a hybrid of the metal and elastic stents, which offers optimal characteristics for the management of diseased airways. In the furtherance of this and other objectives, a stent is provided that has a shape-memory frame that is sufficiently covered with a thin coating so as to prevent epithelialization.

An additional objective of an exemplary device in accordance with the present invention is to provide a prosthesis that is suitable for use in other anatomical locations within a patient such as, by way of example only and not to be construed as limiting, the colon, the billiary tract, the urinary tract, etc., without departing from the basic product design and method manufacture and implantation contemplated by the present invention.

A principal objective of a preferred embodiment of the present invention is to provide a stent that may be stamped from preferably a single material that is capable of maintaining its axial working length when radially compressed. To this end, the stent does not have a seam that could aggravate luminal tissue.

It is yet another objective of an exemplary embodiment of the present invention to provide a stent that can be indicated for the treatment of benign and malignant disease and improve the way clinicians treat malignant airway obstruction.

Still another objective of the present invention is to provide a stent and method for installing the stent that is economical and suitable for routine purposes. In the furtherance of this and other objectives, the stent will be self-expanding and have the ability to be placed through a flexible bronchoscope under local anesthesia in the outpatient setting. Moreover, the stent will have minimal migration, cause minimal tissue granulation, will not foreshorten after deployment and mucociliary clearance will not be problematic.

Yet another objective of an exemplary embodiment in accordance with the present invention is to provide a prosthesis that will have superior internal to external diameter ratio, superior radial force with dynamic expansion, while being suitable for use in pediatric and adult patients with malignant and benign disease.

An additional objective in accordance with an exemplary embodiment of the present invention is to provide a removable self-expanding stent, formed of shape-memory material, which has the ability to be integrated with an antimicrobial agent thus dramatically reducing the incidence of infection.

In the furtherance of this and other objectives, the antimicrobial agent can be coupled with the shape-memory material and/or the polymeric anti-epithilializing material that is associated with the shape-memory material.

Another objective in accordance with a preferred embodiment of the present invention is to provide a method of use, method of manufacture and a stent appropriately configured to serve as a targeted delivery device for chemotherapeutic agents so as to deliver the chemotherapeutic agent to sites of choice so as to provide the chemotherapeutic activity, prevent occlusion or both.

A principal objective of an exemplary stent in accordance with the present invention is to provide a family of stents where the relative hardness/softness of regions of the stent can differ from other regions of the stent to provide additional patient comfort and resistance to radial forces.

An additional objective in accordance with an exemplary embodiment is to provide a family of stents with novel interstice configurations that facilitate flexibility, durability and/or proper installation.

Still another objective of a preferred embodiment of the present invention is to provide a self-expanding stent have the above benefits that also defines a plurality of apertures at the termini of the stent for, inter alia, removal of the stent.

Yet another objective in accordance with an exemplary embodiment is to provide a coated stent. In the furtherance of this and other objectives, an exemplary coated still has a coating that is preferably anchored with the stent about the proximal and distal ends and is free floating there between. Moreover, the coating allows for full and independent self-expansion even after being constrained and sterilized on the delivery system. It is an additional characteristic of this objective to provide a coating that does not have to be porous but must be sufficiently durable to remain functional when the stent is flexed, recaptured or deployed.

An additional objective in accordance with a preferred embodiment of the present invention is to provide an uncovered stent that is easily removable and prevents epithelialization. In the furtherance of this and other objectives, the stent is preferably electropolished.

Further objectives, features and advantages of the invention will be apparent from the following detailed description taken in conjunction with the accompanying drawings.

DETAILED DESCRIPTION OF AN EMBODIMENT

Figure 1:
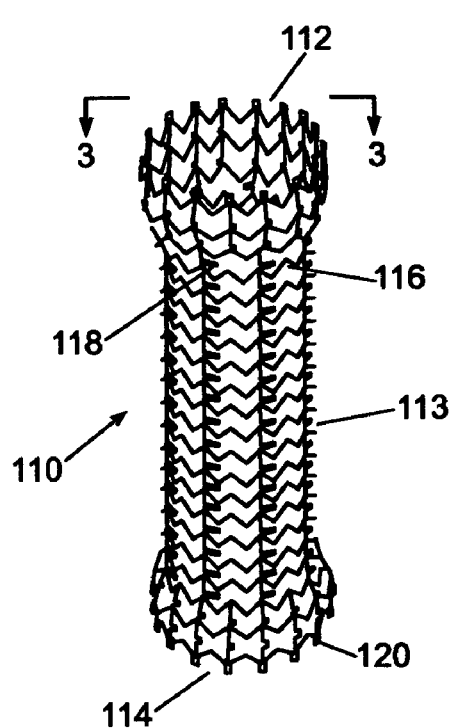
FIG. 1 shows an elevated side perspective view of an exemplary luminal stent in accordance with the present invention.

A preferred embodiment of the stent, in accordance with the present invention, provides a removable stent that prevents epithelialization of the stent and is suitably configured to minimize infections and airway irritation. The exemplary stent is not subject to premature elongation and foreshortening but is capable of engaging the desire implantation location. The stent also retains its axial length while undergoing radial compression. Additionally, the stent has both antimicrobial and/or chemotherapeutic properties so that the stent can be indicated as an early stage therapy.

The term "antimicrobial agent" as used in the present invention means antibiotics, antiseptics, disinfectants and other synthetic moieties, and combinations thereof, that are soluble in organic solvents such as alcohols, ketones, ethers, aldehydes, acetonitrile, acetic acid, formic acid, methylene chloride and chloroform. Classes of antibiotics that can possibly be used include tetracyclines (i.e. minocycline), rifamycins (i.e. rifampin), macrolides (i.e. erythromycin), penicillins (i.e. nafcillin), cephalosporins (i.e. cefazolin), other beta-lactam antibiotics (i.e. imipenem, aztreonam), aminoglycosides (i.e. gentamicin), chloramphenicol, sulfonamides (i.e. sulfamethoxazole), glycopeptides (i.e. vancomycin), quinolones (i.e. ciprofloxacin), fusidic acid, trimethoprim, metronidazole, clindamycin, mupirocin, polyenes (i.e. amphotericin B), azoles (i.e. fluconazole) and beta-lactam inhibitors (i.e. sulbactam).

Examples of specific antibiotics that can be used include minocycline, rifampin, erythromycin, nafcillin, cefazolin, imipenem, aztreonam, gentamicin, sulfamethoxazole, vancomycin, ciprofloxacin, trimethoprim, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, enoxacin, fleroxacin, temafloxacin, tosufloxacin, clinafloxacin, sulbactam, clavulanic acid, amphotericin B, fluconazole, itraconazole, ketoconazole, and nystatin. Other examples of antibiotics, such as those listed in U.S. Pat. No. 4,642,104, herein incorporated by reference, will readily suggest themselves to those of ordinary skill in the art.

Examples of antiseptics and disinfectants are thymol, a-terpineol, methylisothiazolone, cetylpyridinium, chloroxylenol, hexachlorophene, cationic biguanides (i.e. chlorhexidine, cyclohexidine), methylene chloride, iodine and iodophores (i.e. povidone-iodine), triclosan, furan medical preparations (i.e. nitrofurantoin, nitrofurazone), methenamine, aldehydes (glutaraldehyde, formaldehyde) and alcohols. Other examples of antiseptics and disinfectants will readily suggest themselves to those of ordinary skill in the art.

It must also be kept in mind that, though not equivalent, a stent in accordance with the present invention may be prepared with antimicrobial agents in other ways customary in the art. For example, the stent may be made in its entirety or in part of an antimicrobial metal, or at least one surface of the stent may have embedded, by ion beam assisted deposition, therein with atoms of an antimicrobial metal. The antimicrobial metal may include Group II metals. Other suitable examples can be found in the art, for example U.S. Pat. No. 5,520,664, which is incorporated herein by reference. Moreover, chemotherapeutic agents can be coupled with an exemplary stent of the present invention in a manner analogous to that of antimicrobial agents.

Exemplary chemotherapeutic agents include but are not limited to cis-platinum, paclitaxol, 5-flourouracial, gemcytobine and navelbine. The chemotherapeutic agents are generally grouped as DNA-interactive Agents, Antimetabolites, Tubulin-Interactive Agents, Hormonal agents and others such as Asparaginase or Hydroxyurea. Each of the groups of chemotherapeutic agents can be further divided by type of activity or compound. The chemotherapeutic agents used in combination with the anti-cancer agents or benzimidazoles of this invention include members of all of these groups. For a detailed discussion of the chemotherapeutic agents and their method of administration, see Dorr, et al, *Cancer Chemotherapy Handbook*, 2d edition, pages 15-34, Appleton & Lange (Connecticut, 1994) herein incorporated by this reference.

DNA-interactive Agents include the alkylating agents, e.g. Cisplatin, Cyclophosphamide, Altretamine; the DNA strand-breakage agents, such as Bleomycin; the intercalating topoisomerase II inhibitors, e.g., Dactinomycin and Doxorubicin); the nonintercalating topoisomerase II inhibitors such as, Etoposide and Teniposide; and the DNA minor groove binder Plcamydin. The alkylating agents form covalent chemical adducts with cellular DNA, RNA, and protein molecules and with smaller amino acids, glutathione and similar chemicals. Generally, these alkylating agents react with a nucleophilic atom in a cellular constituent, such as an amino, carboxyl, phosphate, or sulfhydryl group in nucleic acids, proteins, amino acids, or glutathione. The mechanism and the role of these alkylating agents in cancer therapy are not well understood. Typical alkylating agents include: Nitrogen mustards, such as Chlorambucil, Cyclophosphamide, Isofamide, Mechlorethamine, Melphalan, Uracil mustard; aziridines such as Thiotepa; methanesulfonate esters such as Busulfan; nitroso ureas, such as Cannustine, Lomustine, Streptozocin; platinum complexes, such as Cisplatin, Carboplatin; bioreductive alkylator, such as Mitomycin, and Procarbazine, Dacarbazine and Altretamine; DNA strand breaking agents include Bleomycin; DNA topoisomerase II inhibitors include the following: Intercalators, such as Amsacrine, Dactinomycin, Daunorubicin, Doxorubicin, Idarubicin, and Mitoxantrone; nonintercalators, such as Etoposide and Teniposide. The DNA minor groove binder is Plicamycin.

The Antimetabolites interfere with the production of nucleic acids by one or the other of two major mechanisms. Some of the drugs inhibit production of the deoxyribonucleoside triphosphates that are the immediate precursors for DNA synthesis, thus inhibiting DNA replication. Some of the compounds are sufficiently like purines or pyrimidines to be able to substitute for them in the anobolic nucleotide pathways. These analogs can then be substituted into the DNA and RNA instead of their normal counterparts. The Antimetabolites useful herein include: folate antagonists such as Methotrexate and trimetrexate pyrimidine antagonists, such as Fluorouracil, Fluorodeoxyuridine, CB3717, Azacytidine, Cytarabine, and Floxuridine purine antagonists include Mercaptopurine, 6-Thioguanine, Fludarabine, Pentostatin; sugar modified analogs include Cyctrabine, Fludarabine; ribonucleotide reductase inhibitors include Hydroxyurea.

Tubulin Interactive agents act by binding to specific sites on Tubulin, a protein that polymerizes to form cellular microtubules. Microtubules are critical cell structure units. When the interactive agents bind on the protein, the cell cannot form microtubules Tubulin Interactive agents include Vincristine and Vinblastine, both alkaloids and Paclitaxel.

Hormonal agents are also useful in the treatment of cancers and tumors. They are used in hormonally susceptible tumors and are usually derived from natural sources. These include: estrogens, conjugated estrogens and Ethinyl Estradiol and Diethylstilbestrol, Chlorotrianisene and Idenestrol; progestins such as Hydroxyprogesterone caproate, Medroxyprogesterone, and Megestrol; androgens such as testosterone, testosterone propionate; fluoxymesterone, methyltestosterone; Adrenal corticosteroids are derived from natural adrenal cortisol or hydrocortisone. They are used because of their anti-inflammatory benefits as well as the ability of some to inhibit mitotic divisions and to halt DNA synthesis. These compounds include Prednisone, Dexamethasone, Methylprednisolone, and Prednisolone.

Leutinizing hormone releasing hormone agents or gonadotropin-releasing hormone antagonists are used primarily the treatment of prostate cancer. These include leuprolide acetate and goserelin acetate. They prevent the biosynthesis of steroids in the testes.

Antihormonal antigens include antiestrogenic agents such as Tamosifen, antiandrogen agents such as Flutamide; and antiadrenal agents such as Mitotane and Aminoglutethimide. Hydroxyurea appears to act primarily through inhibition of the enzyme ribonucleotide reductase. Asparaginase is an enzyme that converts asparagine to nonfunctional aspartic acid and thus blocks protein synthesis in the tumor.

While the foregoing represents some preferred embodiments of the present invention, other antimicrobial and chemotherapeutic agents and coating techniques may be utilized.

A preferred embodiment of a stent of the present invention is made of a shape-memory material such as nickel titanium (nitinol). A tracheal stent, in accordance with the present invention, has a substantially D shaped scaffolding to accommodate the trachea, which has stiff cartilaginous C rings that form the anterior and side walls of this organ while the posterior wall is elastic. The shape-memory material frame may be stamped into a variety of patterns such as that disclosed in German Pat. No. DE-199-06-956, herein incorporated in its entirety by reference.

The frame may be coated with a thin coating (preferably silicone, polyurethane or comparable material adaptable by one skilled in the art) to the extent sufficient to prevent the stent from becoming epithelialized and facilitating removal. In a preferred embodiment, the coating is coupled with the stent about the proximal and/or distal ends and is not anchored to the stent there between. The coating may be porous, but is not required to be. Rather it is preferable that the coating be sufficiently durable to remain functional when the stent is flexed, recaptured or deployed. Moreover, the material from which the coating is selected is limited only by the requirement that the coating allow for full and independent self-expansion even after being constrained and sterilized on the delivery system. It must also be noted that the stent may alternatively be polished. The polishing step facilitates removal of the stent and helps to prevent epithelialization. As a result the polished stent may be used with or without the above referenced coating. The polishing process comprises an electrical polishing process that produces a polished stent wall thickness to a range of about 175 μm-220 μm, and preferably 205 μm, which is about 40% thinner and reduces radial force by 50% with respect to conventional stents. Additionally, the present polishing process provides for a proportional decrease of radial force radial force as wall thickness decreases.

The ends of the stent may be configured to have flanges to prevent migration. In an embodiment having flanges, the ends of each flange are tapered slightly back into the airway thus preventing the ends of the stent from irritating the airway wall. However, providing a stent that is capable of retaining its axial working length while undergoing radial compression also prevents migration. As a result, the stent is more flexible and comfortable since the diameter of the stent can be increased without shortening the stent. Moreover, the resiliency of the stent can be varied over the length and/or cross-section of the stent. Moreover, suture holes are provided so that suture may be used as an anchor to facilitate removal of the stent. To this end, the stent may be deployed with or without suture already coupled with the stent.

An exemplary bronchial stent, in accordance with the present invention, will have similar features as the tracheal stent except that it is substantially tubular in shape. Though the stents are not equivalent, in view of the present disclosure, one of ordinary skill in the art would be able to make the necessary modifications to provide an exemplary tracheal stent.

It should also be kept in mind that though the present discussion has principally focused on airway stents, the device and methods of the present invention are useful in a wide variety of locations within a patient, for example but not limited to the esophagus, trachea, colon, billiary tract, urinary tract and vascular system. They are particularly advantageous for reliably delivering suitable therapeutic agents. In fact, a stent in accordance with the present invention can be configured to serve as a chemotherapeutic and/or antimicrobial agent targeted delivery system suitable for use in a variety of other lumens throughout the anatomy of a patient.

An advantage of the manufacturing process for stents in accordance with the present invention is the ability to modify the relative hardness/softness of regions of the stent. In particular any given region of the stent can differ from other regions of the stent to provide additional patient comfort and resistance to radial forces. This is preferably achieved by changing the relative geometries of the stent scaffolding interstices. In particular, by changing the height and/or width of the loop interstices, relative hardness/softness and radial strength can be adjusted. Moreover, the ability of the stent to flex and resist torsional strain can be enhanced by these interstice adjustments. It should be noted that the present inventors have discovered that all of the above-enumerated features may be incorporated in a bronchial Y-stent. Moreover, unlike conventional Y-stents that are either rubber and/or comprise a modular configuration of parts, a Y-stent in accordance with the present invention is a unitary self-expanding memory metal construction.

Figure 4:
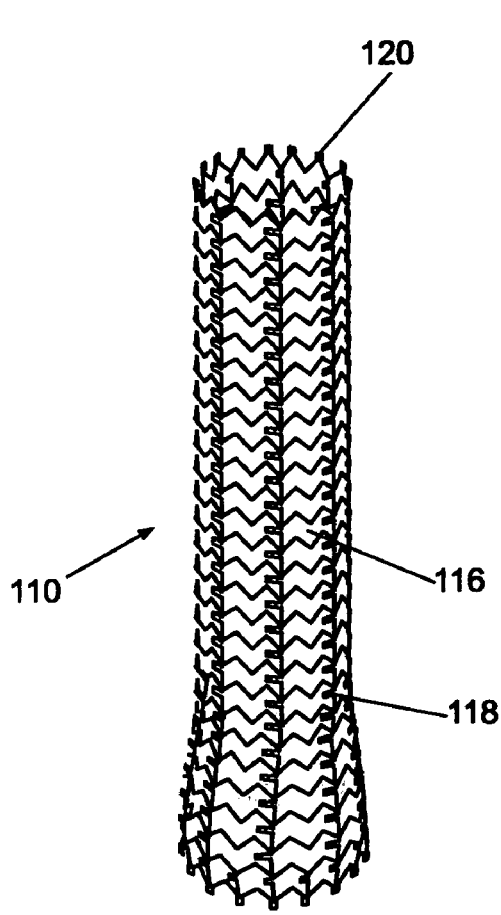
FIG. 4 shows an elevated side perspective view alternative embodiment of a luminal stent in accordance with the present invention.

Turning now to the figures where like numerals refer to like components, of exemplary appliances in accordance with the present invention, the medical appliances are referred to generally with reference numerals 110, 210 and 310. Referring particularly to FIGS. 1-5, a medical appliance 110, is provided that has a unitary memory metal construction. The appliance 110 itself, defines a lumen there through which extends the longitudinal distance of the appliance 110 from the proximal end 112 to the distal end 114. The appliance 110 is preferably a luminal stent having a middle section 113 of a defined diameter that is dimensionally narrower than the defined diameter at the proximal end 112 and/or the distal end 114. FIG. 4 shows a luminal stent in accordance with the present invention that has a flared distal end 114 but not a flared proximal end 112. The appliance can be configured to have the opposite ends flared or no flared ends at all. The luminal stent also is formed of memory metal and preferably has unique geometrical interstices 116 laser etched therein. However, other conventional ways of forming interstices in unitary stents, though not equivalent, are contemplated, may be employed and would be within the skill set of one in the art.

It cannot be overemphasized, however, that this does not mean the knowledge that changes in the geometry of interstices 116 affect stent functionality is currently known in the art. To the contrary, the present inventors discovered the interrelation between interstice geometry, width, length and relative resistance to torsional stress and radial force. In fact, it can be said that the luminal stent 110 has circumferential bands extending perpendicularly with respect to the luminal device's longitudinal axis. A connector 118 connects these bands to one another; the connector 118 is an additional means for adjusting stent functionality. In particular, the connector 118 defines a substantially U shaped member.

Figure 2:
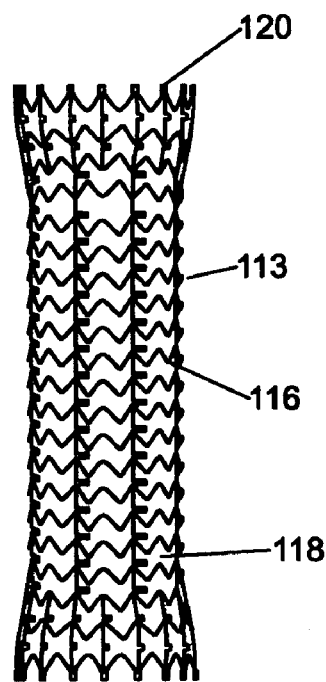
FIG. 2 shows a side perspective view of the luminal stent shown in FIG. 1.
Figure 3:
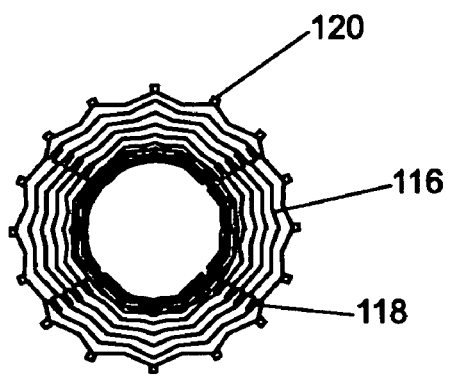
FIG. 3 shows an aerial perspective view of interior of the luminal stent shown in FIG. 1.
Figure 5:
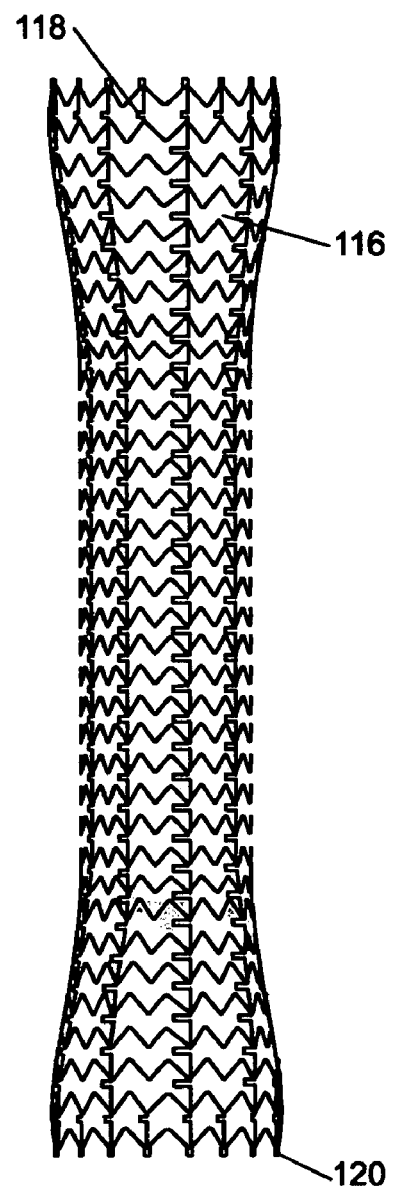
FIG. 5 shows a side perspective view of an alternative embodiment of an exemplary luminal stent in accordance with the present invention.
Figure 6:
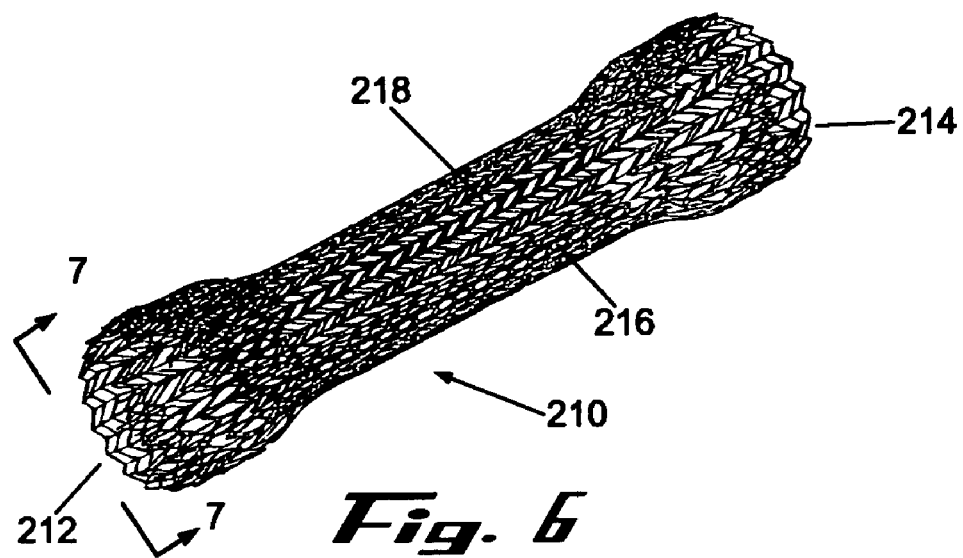
FIG. 6 shows an elevated perspective view of an alternative embodiment of an exemplary luminal stent in accordance with the present invention.
Figure 7:
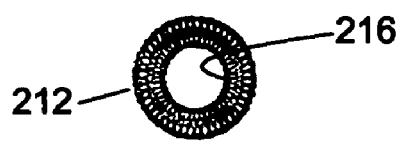
FIG. 7 shows an aerial perspective view through the interior of the luminal stent shown in FIG. 6.
Figure 8:
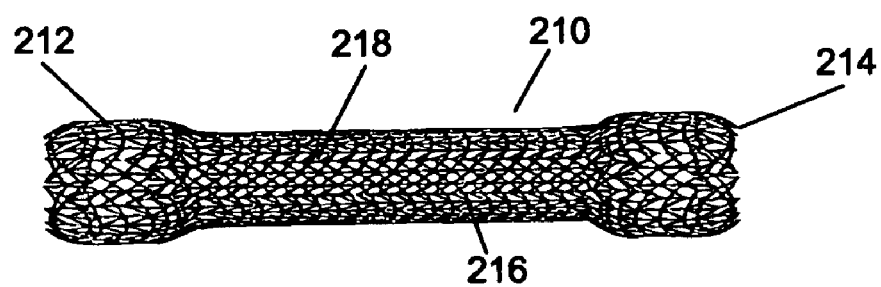
FIG. 8 shows a side perspective view of the luminal stent shown in FIG. 6.
Figure 9:
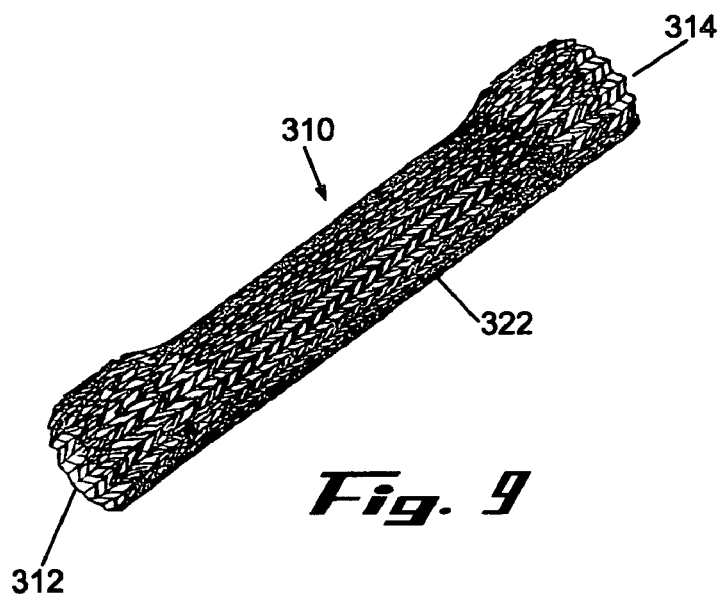
FIG. 9 shows a perspective view showing the longitudinal expanse of the D-shaped configuration of a tracheal appliance in accordance with the present invention.
Figures 10, 11:
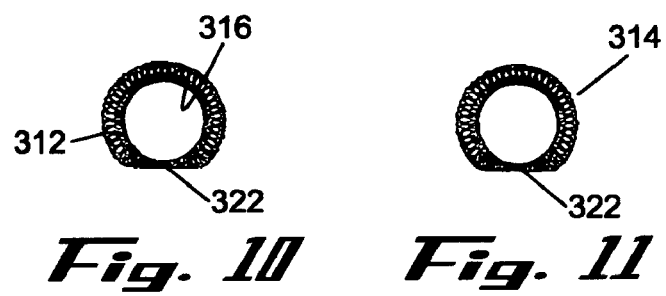
FIG. 10 shows an end view of an exemplary D-shaped tracheal appliance, in accordance with the present invention, showing the external shape of the appliance.
FIG. 11 shows an end view of an exemplary D-shaped tracheal appliance, in accordance with the present invention, looking down the lumen between the distal and proximal ends thereof.
Figure 12:
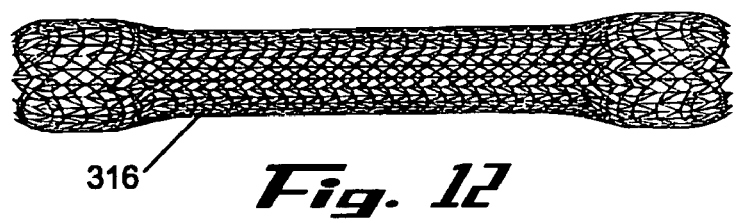
FIG. 12 shows an aerial perspective view of the top surface of the D-shaped tracheal appliance shown in FIG. 9.
Figure 13:
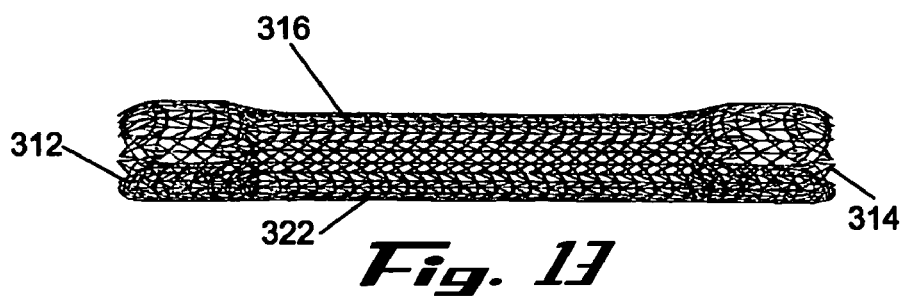
FIG. 13 shows a side perspective view of an exemplary embodiment of a medical appliance, in accordance with the invention shown in FIG. 9, wherein the D-shaped appliance is resting on its substantially flat surface.
Figure 14:
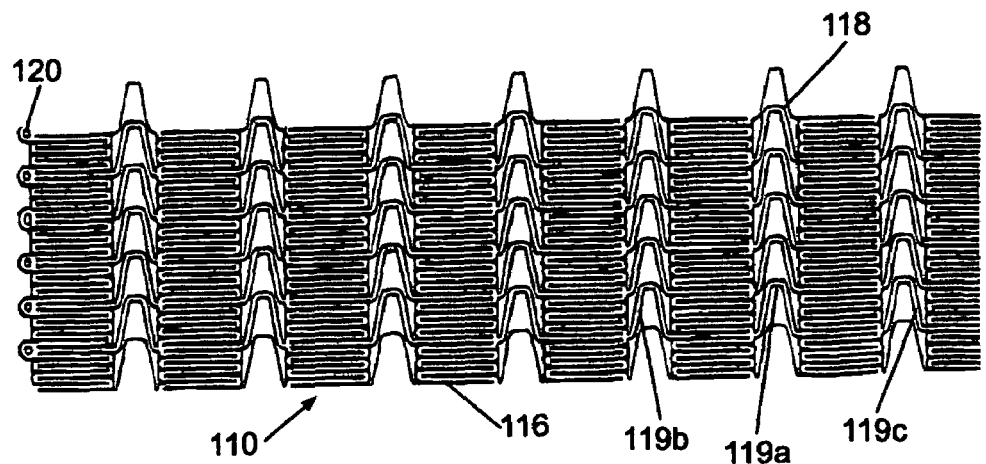
FIG. 14 shows a magnified view of the scaffolding and interstice topology of the medical appliance shown in FIG. 1.

As can be seen in FIGS. 2, 5 and 14, for example, the plurality of expandable circumferential bands of the appliance 110 are formed of struts having interconnected ends, which define a series of alternating peaks and valleys. The peaks and valleys of adjacent circumferential bands are in-phase except for at least one out-of-phase pair of circumferential bands. In FIG. 2, three pairs of circumferential bands are illustrated as being out-of-phase, and in FIGS. 5 and 14, one pair of circumferential bands is illustrated as being out-of-phase. A plurality of the flexible connectors 118 extend between each pair of the circumferential bands, and at least one set of the flexible connectors extends between and connects at least one pair of peaks or one pair of valleys of the out-of-phase pair of circumferential bands. The distal end 114 of the cylindrical member is defined by a circumferential band connected to flexible connectors 118 that extend only in the proximal direction, and the proximal end 112 of the cylindrical member is defined by a circumferential band connected to flexible connectors that extend only in the distal direction.

In a standard orientation, the substantially U-shape comprises preferably two leg members and a crossing member that connects with and extends perpendicularly at a 90° angles with respect to the leg members. The present inventors discovered that if you modify the length of the crossing member and/or the leg members and/or the angle at which the crossing member and the leg members intersect, the relative hardness/softness of the stent could be modified. The angles can be modified at varying acute angles short of 90°. The incremental changes correspondingly change certain characteristics of the stent. As a result, different regions of the luminal stent 110 can be given different rigidities to improve patient comfort and to facilitate luminal patency. Moreover, various anatomical lumens may need different degrees of stent rigidity. As a result, stents in accordance with the present invention can be manufactured to exacting specifications to contour properly to various lumens in a patient's anatomy, which may need varying levels of structural support from the medical appliance.

Figure 15:
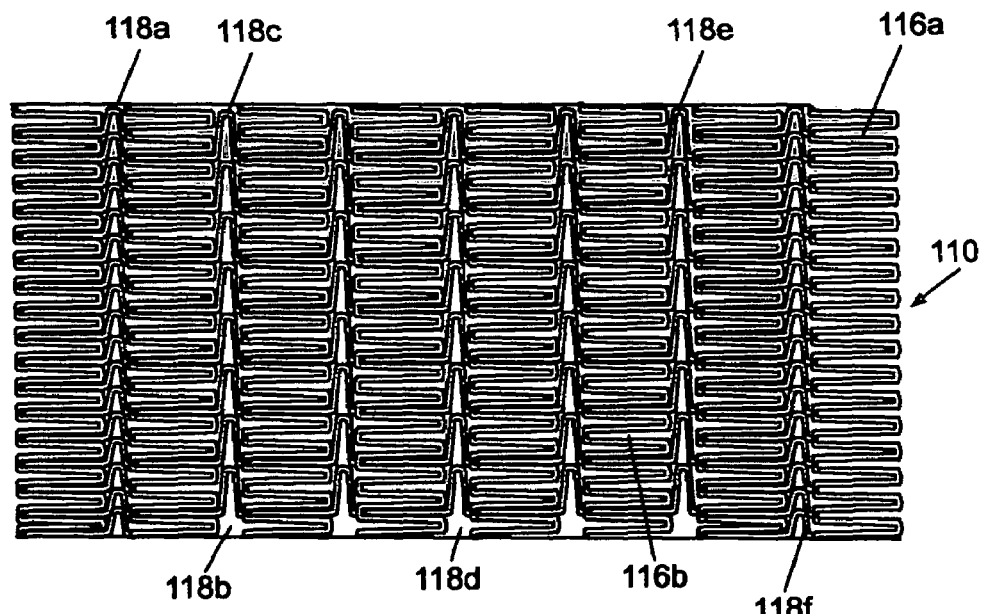
FIG. 15 shows a magnified portion of the scaffolding and interstice topology of the medical appliance of FIG. 1, showing how modifications in geometric dimensions affect functionality.

Referring now to FIGS. 14 and 15, luminal stent 110 is shown having substantially U shaped connectors 118 having a crossing member 119a and at least two leg members 119b-c respectively. The present inventors discovered that if you increase/decrease the length of leg members 119b and/or 119c, increase/decrease the length of crossing member 119a, and/or vary the angle at which crossing member 119a and leg members 119b-c intersect, you affect the functionality of the stent. In particular, the shorter the length of leg members 119a-b the less flexibility available in that portion of the stent. Taking particular note of FIG. 15, by way of example only, if you want to decrease the amount of torsional flexibility of the luminal stent 110, you would have to modify the desired portion of the stent to resemble 118f. However, if you want a stiffer appliance 110, you would have a configuration analogous to that of 118a.

In a preferred embodiment, the modification of interstice geometries' and manipulation of the U shaped connection member to achieve variable stent functionality is provided. The rigidity of the stent scaffolding or interstice matrix along with the torsionality of the stent itself is principally a function of these modifications. In an exemplary embodiment, the stents relative flexibility can be rated soft, medium or hard based on the degree of flex and torsionality. The less torsionality and flex in the stent the harder the stent is rated.

An exemplary stent in accordance with the present invention with relatively great torsionality and radial flexibility would be rated soft. An exemplary soft rated stent comprises distance between U shaped connectors of about 4.5 µm in the compressed state (i.e., contracted in the 3 mm tube subject to laser etching). Moreover, the length of the crossing member is preferably about 1.0 µm. The lengths of the leg members are preferably about 1.5 µm in length. Additionally the leg members may further comprise feet that attached to the remainder of the stent scaffolding. The feet can be adjusted from a standard length of about 0.25 µm to further adjust the characteristics of the stent. There is additionally a substantially rectangular member incorporated in the U shaped connector with similar capacity for variability. The variability factors and results of modifying the dimensions of the substantially rectangular members are similar to those evinced by leg length dimensional modifications.

By way of example, but not to be construed in any way as limiting, the softness index or relative flexibility can be increase by increasing the various lengths discussed above. For example, by increasing the length of the legs and crossing members of the U shaped connector, flexibility increases. However, with respect to the distance between U shaped members and distance between interstices in a preferred stent embodiment, there is an inverse correlation between length and softness. This relative softness/hardness indexing as a corollary of interstice dimensions is a novel aspect of preferred embodiment of the present invention. As a practical rule of thumb, longer leg lengths coupled with acute angles provide for greater flexibility. Conversely, shorter leg lengths and more obtuse angles provide more rigidity. By way of non-limiting example, a U shaped connector with short legs deviating from the crossing member at angles greater than 90°, will be extremely rigid and resistant to torsional strain as compared to a U shaped connector with longer legs diverging from the crossing member at angles less than 90°.

In addition to the length and spacing differences, the interstices themselves may define various shapes that by their very nature afford novel functionality to the stent. The changes of functionality, however, are more a function of the dimensional differences of the various shapes rather than a function of the shapes themselves. Therefore, it is important to keep in mind that the dimensional differences discussed in the previous paragraph are determinative of the functionality accorded the stent by the varying interstice geometries. It is for this reason that one of ordinary skill in the art, after being apprised of the present invention, would be able to conceive of a number of interstice geometries to satisfy certain functionality criteria by keeping certain dimensional parameters constant.

Figure 16:
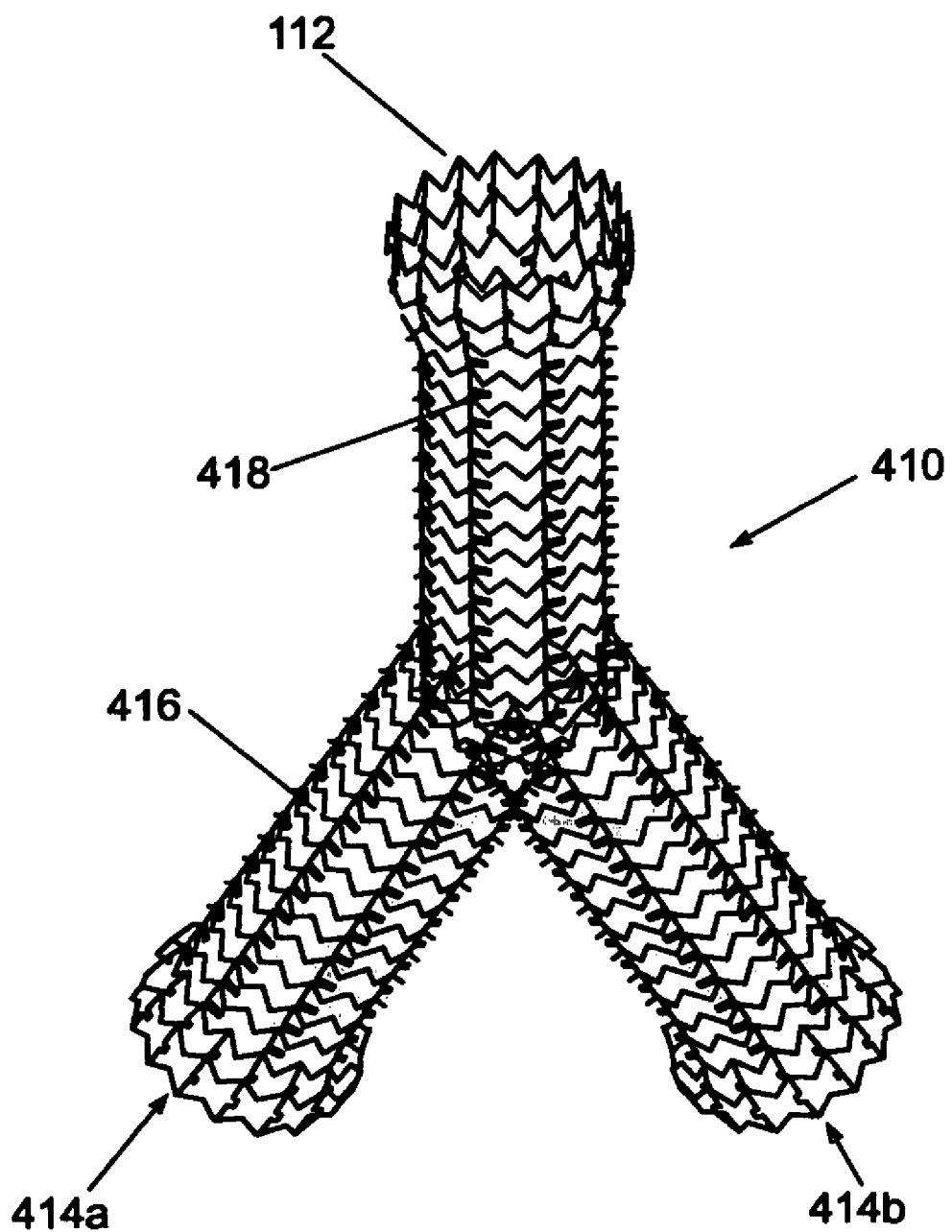
FIG. 16 shows an elevated side perspective view of an exemplary Y-stent luminal stent in accordance with the present invention.

Referring now to FIG. 16, an exemplary Y-shaped stent 410 is shown that exemplifies the characteristics of luminal stents 110, 210 and 310. The Y-shaped stent also incorporates the advantages discussed above, including but not limited to, interstice geometrical advantages, polishing advantages, inward extending termini, suture apertures, antimicrobial and chemotherapeutic agent delivery, coating, etc.

In a preferred embodiment of a luminal stent in accordance with the present invention as shown in FIGS. 1-5, the proximal end 112 and the distal end 114 defines a plurality of apertures 120 for receiving suture. The luminal stent 110 may be deployed with or without suture engaged to facilitate the stent removal process.

As discussed above, a preferred luminal stent 110 further comprises a coating (not shown), which preferably extends the substantially the entire distance of the luminal stent 110. In particular, in a preferred embodiment the luminal stent is coated from about the proximal end 112 to the distal end 114, inclusive of suture apertures 120. Moreover, it is preferable that the coating is coupled with the luminal stent 110 about the proximal end 112 and distal end 114. The coating may be coupled to the luminal stent 110 by any number of adhesion systems available in the art. The principal requirement is that adhesive sufficiently couple the coating with luminal stent 110 so as to withstand the pressures of stent deployment, expansion, flexing and removal.

As an alternative, and in other embodiments in addition to, the coating an exemplary luminal stent 110 is electropolished to remove rough edges and to create a thinner more resilient appliance. In particular, the electrical polishing process produces a polished luminal stent wall thickness in the optimal range of about 175 μm-220 μm, and preferably 205 μm, which is about 40% thinner and reduces radial force by 50% with respect to conventional stents. Conventional stent polishing methods comprise a fluid abrasive media extruded through an apparatus in abrading contact with inner and outer surfaces and circumferential openings of a stent. As a result, conventional stent polishing methods are incapable of polishing stents to an optimal thickness that allows the stent to demonstrate characteristics of a covered stent in accordance with the present invention, namely, epithelialization retardation, enhanced removability, etc. As shown in Table 1, a polished stent in accordance with the present invention demonstrates desirable stent wall thickness, which is not achievable with shaping or staining processes. Moreover, standard polishing processing cannot achieve the desired stent wall thickness without compromising the integrity of the memory metal alloy and its shape memory characteristics.

TABLE 1

| Condition | Wall Thickness (μm) | $F_{max}$ (Mean value)(mN) | Standard Deviation (mN) |
| --- | --- | --- | --- |
| Shaped | 250 | 2733 | 296 |
| Stained | 233 | 1848 | 165 |
| Polished | 205 | 1518 | 53 |

The reduced radial force extends the useful life of the luminal stent 110 while also reducing significantly the pressure the stent exerts on the luminal tissue. It has been determined that as stent wall thickness decreases radial force decreases as well. The optimal range is an important discovery since it allows for the design of a luminal stent 110 that achieves optimal stent migration prevention while exerting minimal pressure on the surrounding luminal tissue.

The radial strength of the stent is defined as the change of the diameter of the stent as a function of applied surrounding pressure once the stent is deployed. The greater the radial strength of the stent, the more the appliance will resist deformation as a result of the forces imposed on the stent by the lumen. Radial strength of stents can generally be tested by conventional methods known in the art, such as DH Kim et al., Korean J. Radiology, June 2001; 2:75-79.

Luminal stents 210 and 310 in accordance with the present invention are shown in FIGS. 6-13 showing alternative interstice geometries. Not shown are a wide variety of interstice geometries that are also acceptable alternatives to the preferred, V, W, Z, S and X geometries claimed herein. Moreover, FIGS. 9-13 shows luminal stent 310 that has a substantially flat side 322 that extends longitudinally between proximal end 312 and distal end 314. As pointed out above, though stents 210 and 310 are shown with flared proximal ends 212 & 312 and distal ends 214 & 314, respectively, flared ends are not necessary. It should also be pointed out with respect to the respective ends of luminal stents 110, 210 and 310; proximal 112, 212 & 312 and distal ends 114, 214 & 314 preferably orient inward towards its lumen. In particular, it is preferable that suture apertures 120, 220 & 320 extend away from the lumen of the tissue of the patient and toward one another.

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes, which come within the meaning and range of equivalency of the claims, are to be embraced within their scope.

What is claimed is:

1. A medical appliance for placement within and removal from a portion of the anatomy of a patient, the appliance comprising:

a scaffolding, the scaffolding configured to define a substantially cylindrical member having a distal end and a proximal end and extending longitudinally there between, forming a lumen there through, such that when pressure is exerted along varying points of the longitudinal extension of the appliance, the appliance does not undesirably foreshorten or elongate, said scaffolding comprising:

a plurality of expandable circumferential bands formed of struts having interconnected ends defining a series of alternating peaks and valleys, said peaks and valleys of adjacent circumferential bands being in-phase except for at least one out-of-phase pair of circumferential bands, and a plurality of flexible connectors extending between each pair of the circumferential bands, wherein at least one set of the flexible connectors extends between and connects at least one pair of peaks or one pair of valleys of the out-of-phase pair of circumferential bands, wherein, each of the plurality of connectors are spaced apart from one another by at least one pair of peaks and one pair of valleys of adjacent circumferential bands, and further wherein the distal end of the cylindrical member is defined by a circumferential band connected to flexible connectors that extend only in the proximal direction, and the proximal end of the cylindrical member is defined by a circumferential band connected to flexible connectors that extend only in the distal direction.

2. The medical appliance of claim 1, wherein the medical appliance comprises at least three circumferential bands and a plurality of flexible connectors extending therebetween, and wherein a pair of the flexible connectors extending between adjacent circumferential rows are in axial alignment with one another.

3. A medical appliance for placement within and removal from a portion of the anatomy of a patient, the appliance comprising:

a scaffolding, the scaffolding configured to define a substantially cylindrical member having a distal end and a proximal end and extending longitudinally there between, forming a lumen there through, such that when pressure is exerted along varying points of the longitudinal extension of the appliance, the appliance does not undesirably foreshorten or elongate, wherein along the longitudinal extension of the appliance, the scaffolding forms geometrical patterns, said scaffolding comprising:

a plurality of expandable circumferential bands formed of struts having interconnected ends defining a series of alternating peaks and valleys, said peaks and valleys of adjacent circumferential bands being in-phase except for at least one out-of-phase pair of circumferential bands, and a plurality of flexible connectors extending between each pair of the circumferential bands, wherein at least one set of the flexible connectors extends between and connects at least one pair of peaks or one pair of valleys of the out-of-phase pair of circumferential bands, each of the flexible connectors including a substantially U-shaped connector member coupled with portions of the geometrical patterns, the U-shaped connector comprising a crossing member and a plurality of leg members extending from the crossing member, wherein the length of the leg members and the degree of the angle at which the legs extend from the crossing member determines the relative flexibility of the medical appliance, wherein, each of the plurality of connectors are spaced apart from one another by at least one pair of peaks and one pair of valleys of adjacent circumferential bands, and further wherein the distal end of the cylindrical member is defined by a circumferential band connected to flexible connectors that extend only in the proximal direction, and the proximal end of the cylindrical member is defined by a circumferential band connected to flexible connectors that extend only in the distal direction.

4. The medical appliance of claim 3, wherein the angle at which the leg members extend from the crossing member is greater than about 90°.

5. The medical appliance of claim 4, wherein the medical appliance is relatively rigid.

6. The medical appliance of claim 3, wherein the angle at which the leg members extend from the crossing member is about 90° or less.

7. The medical appliance of claim 6, wherein the medical appliance is relatively flexible.

8. A medical appliance for placement within and removal from a portion of the anatomy of a patient, the appliance comprising:

a scaffolding, the scaffolding configured to define a substantially cylindrical member having a distal end and a proximal end and extending longitudinally there between, forming a lumen there through, such that when pressure is exerted along varying points of the longitudinal extension of the appliance, the appliance does not undesirably foreshorten or elongate, wherein the thickness of the scaffolding is about between 150 μm and 220 μm said scaffolding comprising:

a plurality of expandable circumferential bands formed of struts having interconnected ends defining a series of alternating peaks and valleys, said peaks and valleys of adjacent circumferential bands being in-phase except for at least one out-of-phase pair of circumferential bands, and a plurality of flexible connectors extending between each pair of the circumferential bands, wherein at least one set of the flexible connectors extends between and connects at least one pair of peaks or one pair of valleys of the out-of-phase pair of circumferential bands, wherein, each of the plurality of connectors are spaced apart from one another by at least one pair of peaks and one pair of valleys of adjacent circumferential bands, and further wherein the distal end of the cylindrical member is defined by a circumferential band connected to flexible connectors that extend only in the proximal direction, and the proximal end of the cylindrical member is defined by a circumferential band connected to flexible connectors that extend only in the distal direction.

9. The medical appliance in accordance with claim 8, wherein the scaffolding thickness is about between 175 μm and 210 μm.

10. The medical appliance of claim 9, wherein the thickness of the scaffolding is about between 195 μm and 205 μm.

11. The medical appliance of claim 10, wherein the scaffolding thickness is about 205 μm.

12. A method of treating a patient suffering from luminal irregularities, comprising the steps of:

providing a medical appliance comprising a scaffolding, the scaffolding configured to define a substantially cylindrical member having a distal end and a proximal end and extending longitudinally there between, forming a lumen there through, such that when pressure is exerted along varying points of the longitudinal extension of the appliance, the appliance does not undesirably foreshorten or elongate, said scaffolding comprising:

a plurality of expandable circumferential bands formed of struts having interconnected ends defining a series of alternating peaks and valleys, said peaks and valleys of adjacent circumferential bands being in-phase except for at least one out-of-phase pair of circumferential bands, and a plurality of flexible connectors extending between each pair of the circumferential bands, wherein at least one set of the flexible connectors extends between and connects at least one pair of peaks or one pair of valleys of the out-of-phase pair of circumferential bands, wherein each of the plurality of connectors are spaced apart from one another by at least one pair of peaks and one pair of valleys of adjacent circumferential bands, and further wherein the distal end of the cylindrical member is defined by a circumferential band connected to flexible connectors that extend only in the proximal direction, and the proximal end of the cylindrical member is defined by a circumferential band connected to flexible connectors that extend only in the distal direction;

installing the medical appliance in a non-vascular lumen of the patient;

activating the expansion of the medical appliance in the desired location; and removing the medical appliance from the lumen of the patient.

13. A medical appliance for placement within and removal from a portion of the anatomy of a patient, the appliance comprising:

an electropolished scaffolding, the scaffolding configured to define a substantially cylindrical member having a distal end and a proximal end and extending longitudinally there between, forming a lumen there through, such that when pressure is exerted along varying points of the longitudinal extension of the appliance, the appliance does not undesirably foreshorten or elongate, said scaffolding comprising:

a plurality of expandable circumferential bands formed of struts having interconnected ends defining a series of alternating peaks and valleys, said peaks and valleys of adjacent circumferential bands being in-phase except for at least one out-of-phase pair of circumferential bands, and a plurality of flexible connectors extending between each pair of the circumferential bands, wherein at least one set of the flexible connectors extends between and connects at least one pair of peaks or one pair of valleys of the out-of-phase pair of circumferential bands, wherein, each of the plurality of connectors are spaced apart from one another by at least one pair of peaks and one pair of valleys of adjacent circumferential bands, and further wherein the distal end of the cylindrical member is defined by a circumferential band connected to flexible connectors that extend only in the proximal direction, and the proximal end of the cylindrical member is defined by a circumferential band connected to flexible connectors that extend only in the distal direction and, wherein the scaffolding is electropolished.

14. The medical appliance of claim 13, wherein along the longitudinal extension of the appliance, the scaffolding forms geometrical patterns.

15. The medical appliance of claim 14, wherein the dimensions of the scaffolding geometry determine torsionality of the medical appliance.

16. The medical appliance of claim 14, further comprising a substantially U-shaped connector member coupled with portions of the geometrical patterns, the U-shaped connector comprising a crossing member and a plurality of leg members extending from the crossing member.

17. The medical appliance of claim 16, wherein the substantially U-shaped connector further comprises a rectangular detent extending from a leg thereof.

18. The medical appliance of claim 16, wherein the length of the leg members and the degree of the angle at which the legs extend from the crossing member determines the relative flexibility of the medical appliance.

19. The medical appliance of claim 18, wherein the angle at which the leg members extend from the crossing member is greater than about 90°.

20. The medical appliance of claim 19, wherein the medical appliance is relatively rigid.

21. The medical appliance of claim 18, wherein the angle at which the leg members extend from the crossing member is about 90° or less.

22. The medical appliance of claim 21, wherein the medical appliance is relatively flexible.

23. The medical appliance of claim 14, wherein the geometrical patterns are substantially W-shaped.

24. The medical appliance of claim 14, wherein the geometrical patterns are substantially V-shaped.

25. The medical appliance of claim 14, wherein the geometrical patterns are substantially Z-shaped.

26. The medical appliance of claim 14, wherein the geometrical patterns are substantially S-shaped.

27. The medical appliance of claim 14, wherein the geometrical patterns are substantially X-shaped.

28. The medical appliance of claim 13, wherein the scaffolding is formed of a memory capable alloy.

29. The medical appliance of claim 28, wherein the memory capable alloy has antimicrobial properties.

30. The medical appliance of claim 29, wherein the antimicrobial alloy is selected from the group consisting of group eleven metals.

31. The medical appliance of claim 13, wherein near the distal and proximal ends of the scaffolding the medical appliance further comprise a plurality of flanges that define apertures there through.

32. The medical appliance of claim 13, wherein the scaffolding further comprises an antimicrobial agent coupled therewith.

33. The medical appliance of claim 32, wherein the antimicrobial agent is selected from the group consisting of tetracyclines, rifamycins, macrolides, penicillins, cephalosporins, p-lactam antibiotics, aminoglycosides, chloramphenicols, sulfonamides, glycopeptides, quinolones, fluidic acid, trimethoprim, metornidazole, clindamycin, mupirocin, polyenes, azoles, and beta-lactam inhibitors.

34. The medical appliance of claim 13, wherein the scaffolding further comprises an antiseptic or disinfectant coupled therewith.

35. The medical appliance of claim 34, wherein the antiseptic or disinfectant is selected from the group consisting of thymol, .alpha.-terpineol, methylisothiazolone, cetylpyridinium, chloroxylenol, hexachlorophene, cationic biguanides, methylene chloride, iodine and iodophores, triclosan, furan medical preparations, methenamine, aldehydes and alcohols.

36. The medical appliance of claim 13, wherein the scaffolding may be made in its entirety or in part of an antimicrobial metal.

37. The medical appliance of claim 13, wherein at least one surface of the scaffolding may have embedded, by ion beam assisted deposition, therein with atoms of an antimicrobial metal.

38. The medical appliance of claim 13, wherein the scaffolding further comprises a chemotherapeutic agent coupled therewith.

39. The medical appliance of claim 38, wherein the chemotherapeutic agent is selected from the group consisting of DNA-interactive Agents, Antimetabolites, Tubulin-Interactive Agents, Hormonal agents and others such as Asparaginase or Hydroxyurea.

40. The medical appliance of claim 39, wherein the DNA-Interactive Agents are selected from the group consisting of alkylating agents, the DNA strand-breakage agents, the intercalating topoisomerase II inhibitors, and the nonintercalating topoisomerase H inhibitors.

41. The medical appliance of claim 40, wherein the alkylating agents are selected from the group consisting of Nitrogen mustards, aziridines, nitroso ureas, platinum complexes, bioreductive alkylator, DNA strand breaking agents, Intercalators and nonintercalators.

42. The medical appliance of claim 39, wherein the Antimetabolites are selected from the group consisting of folate antagonists such as Methotrexate and trimetrexate; pyrimidine antagonists, such as Fluorouracil, Fluorodeoxyuridine, CB3717, Azacytidine, Cytarabine; Floxuridine purine antagonists include Mercaptopurine, 6-Thioguanine, Fludarabine, Pentostatin; sugar modified analogs include Cyctrabine, Fludarabine; and ribonucleotide reductase inhibitors include Hydroxyurea.

43. The medical appliance of claim 13, wherein the scaffolding further comprises a hormonal agent coupled therewith.

44. The medical appliance of claim 43, wherein the hormonal agent is selected from the group consisting of estrogens, conjugated estrogens; progestins; and androgens.

45. The medical appliance of claim 13, wherein the scaffolding further comprises an anti-hormonal agent coupled therewith.

46. The medical appliance of claim 45, wherein the anti-hormonal agent is selected from the group consisting of anti-estrogenic, antiandrogen agents, and antiadrenal agents.

47. The medical appliance of claim 46, wherein the thickness of the scaffolding is about between 150 μm and 220 μm.

48. The medical appliance in accordance with claim 47, wherein the scaffolding thickness is about between 175 μm and 210 μm.

49. The medical appliance of claim 48, wherein the thickness of the scaffolding is about between 195 μm and 205 μm.

50. The medical appliance of claim 49, wherein the scaffolding thickness is about 205 μm.

51. A method of treating a patient suffering from luminal irregularities, comprising the steps of:

providing a medical appliance comprising an electropolished scaffolding, the scaffolding configured to define a substantially cylindrical member having a distal end and a proximal end and extending longitudinally there between, forming a lumen there through, such that when pressure is exerted along varying points of the longitudinal extension of the appliance, the appliance does not undesirably foreshorten or elongate, said scaffolding comprising:

a plurality of expandable circumferential bands formed of struts having interconnected ends defining a series of alternating peaks and valleys, said peaks and valleys of adjacent circumferential bands being in-phase except for at least one out-of-phase pair of circumferential bands, and a plurality of flexible connectors extending between each pair of the circumferential bands, wherein at least one set of the flexible connectors extends between and connects at least one pair of peaks or one pair of valleys of the out-of-phase pair of circumferential bands, wherein each of the plurality of connectors are spaced apart from one another by at least one pair of peaks and one pair of valleys of adjacent circumferential bands, and further wherein the distal end of the cylindrical member is defined by a circumferential band connected to flexible connectors that extend only in the proximal direction, and the proximal end of the cylindrical member is defined by a circumferential band connected to flexible connectors that extend only in the distal direction;

installing the medical appliance in a preferred location of the anatomy of the patient; and activating the expansion of the medical appliance in the desired location.

52. The method of claim 51, wherein the preferred location is a non-vascular lumen.

53. The method of claim 52, further comprising the step of removing the medical appliance from the anatomy of the patient.

54. The method of claim 52, wherein the medical appliance further comprises anti-microbial agents coupled therewith.

55. The method of claim 52, wherein the medical appliance further comprises chemotherapeutic agents coupled therewith.

* * * * *